(12) United States Patent
Messerly (10) Patent No.: US 11,918,795 B2
(45) Date of Patent: Mar. 5, 2024

(54) PUNCTURING DEVICES, PUNCTURING SYSTEMS INCLUDING THE PUNCTURING DEVICES, AND METHODS THEREOF

(71) Applicant: Bard Access Systems, Inc., Salt Lake City, UT (US)

(72) Inventor: Shayne Messerly, Kaysville, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 817 days.

(21) Appl. No.: 16/855,840

(22) Filed: Apr. 22, 2020

(65) Prior Publication Data

US 2020/0345950 A1 Nov. 5, 2020

Related U.S. Application Data

(60) Provisional application No. 62/841,501, filed on May 1, 2019.

(51) Int. Cl.
*A61M 5/32* (2006.01)
*A61M 25/06* (2006.01)

(52) U.S. Cl.
CPC ....... *A61M 5/3287* (2013.01); *A61M 25/0693* (2013.01); *A61M 2205/3313* (2013.01); *A61M 2205/52* (2013.01); *A61M 2230/205* (2013.01); *A61M 2230/30* (2013.01); *A61M 2230/65* (2013.01)

(58) Field of Classification Search
CPC ............ A61M 5/3287; A61M 25/0693; A61M 2205/3313; A61M 2205/52; A61M 2230/205; A61M 2230/30; A61M 2230/65; A61M 2205/3306; A61M 25/0606; A61M 2205/3327; A61B 5/14542; A61B 5/1473
See application file for complete search history.

(56) References Cited

U.S. PATENT DOCUMENTS

| | | | |
|---|---|---|---|
| 3,556,079 A | 1/1971 | Omizo | |
| 3,777,740 A | 12/1973 | Hokanson | |
| 3,987,673 A | 10/1976 | Hansen | |
| 4,103,679 A | 8/1978 | Aronson | |

(Continued)

FOREIGN PATENT DOCUMENTS

| | | |
|---|---|---|
| CN | 201076504 Y | 6/2008 |
| CN | 105769303 B | 4/2019 |

(Continued)

OTHER PUBLICATIONS

PCT/US2020/029382 filed Apr. 22, 2020 International Search Report and Written Opinion dated Jul. 6, 2020.

(Continued)

*Primary Examiner* — James D Ponton
(74) *Attorney, Agent, or Firm* — Rutan & Tucker LLP (57) ABSTRACT

Disclosed herein are puncturing devices and puncturing systems including the puncturing devices. Such puncturing devices and systems include those that sense a difference between venous blood and arterial blood as a function of blood oxygen, impedance, or pressure. As a result, the puncturing devices and systems are able to differentiate between a venipuncture and an arterial puncture. Methods of the puncturing devices and systems for differentiating between a venipuncture and an arterial puncture for are also disclosed.

5 Claims, 7 Drawing Sheets

(56) References Cited

U.S. PATENT DOCUMENTS

| | | |
|---|---|---|
| 4,527,569 A | 7/1985 | Kolb |
| 4,672,971 A * | 6/1987 | Otten .................. A61B 5/1473 |
| | | 204/415 |
| 4,787,395 A | 11/1988 | Yanashima et al. |
| 5,121,749 A | 6/1992 | Nassi et al. |
| 5,131,395 A | 7/1992 | Gehlbach |
| 5,167,630 A | 12/1992 | Paul |
| 5,249,577 A | 10/1993 | Shinomura et al. |
| 5,259,386 A | 11/1993 | Sharkawy |
| 5,261,409 A | 11/1993 | Dardel |
| 5,280,787 A | 1/1994 | Wilson et al. |
| 5,363,852 A | 11/1994 | Sharkawy |
| 5,387,329 A | 2/1995 | Foos et al. |
| 5,390,677 A | 2/1995 | Ferrera et al. |
| 5,490,522 A | 2/1996 | Dardel |
| 5,546,807 A | 8/1996 | Oxaal et al. |
| 5,687,729 A | 11/1997 | Schaetzle |
| 5,701,898 A | 12/1997 | Adam et al. |
| 5,910,119 A | 6/1999 | Lin |
| 5,941,825 A | 8/1999 | Lang et al. |
| 6,068,599 A | 5/2000 | Saito et al. |
| 6,132,379 A | 10/2000 | Patacsil et al. |
| 6,171,248 B1 | 1/2001 | Hossack et al. |
| 6,203,498 B1 | 3/2001 | Bunce et al. |
| 6,222,948 B1 | 4/2001 | Hossack et al. |
| 6,293,914 B1 | 9/2001 | Sumanaweera et al. |
| 6,299,583 B1 * | 10/2001 | Eggers .................. A61B 5/412 |
| | | 600/479 |
| 6,336,899 B1 | 1/2002 | Yamazaki |
| 6,423,006 B1 | 7/2002 | Banjanin |
| 6,503,205 B2 | 1/2003 | Manor et al. |
| 6,524,247 B2 | 2/2003 | Zhao et al. |
| 6,616,610 B2 | 9/2003 | Steininger et al. |
| 6,733,458 B1 | 5/2004 | Steins et al. |
| 6,755,789 B2 | 6/2004 | Stringer et al. |
| 6,780,155 B2 | 8/2004 | Li |
| 7,048,691 B2 | 5/2006 | Miele et al. |
| 7,066,887 B2 | 6/2006 | Flesch et al. |
| 7,066,888 B2 | 6/2006 | Abend et al. |
| 7,503,896 B2 | 3/2009 | Miele et al. |
| 7,534,209 B2 | 5/2009 | Abend et al. |
| 7,591,787 B2 | 9/2009 | Tortoli |
| 7,699,776 B2 | 4/2010 | Walker et al. |
| 7,766,839 B2 | 8/2010 | Rogers et al. |
| 7,806,828 B2 | 10/2010 | Stringer |
| 8,012,090 B2 | 9/2011 | Steen |
| 8,052,606 B2 | 11/2011 | Barnes et al. |
| 8,080,424 B2 | 12/2011 | Ghobadi |
| 8,409,094 B2 | 4/2013 | Nakajima et al. |
| 8,679,022 B2 | 3/2014 | Tsuruno |
| 8,764,663 B2 | 7/2014 | Smok et al. |
| 8,861,822 B2 | 10/2014 | Pagoulatos et al. |
| 8,882,671 B2 | 11/2014 | Sasaki et al. |
| 8,956,300 B2 | 2/2015 | Guo et al. |
| 9,022,940 B2 | 5/2015 | Meier |
| 9,566,042 B2 | 2/2017 | Greppi et al. |
| 2004/0002544 A1 | 12/2004 | Herzog et al. |
| 2006/0001840 A1 | 8/2006 | Haim et al. |
| 2007/0001678 A1 | 7/2007 | Nozaki |
| 2008/0000251 A1 | 1/2008 | Peszynski et al. |
| 2008/0001950 A1 | 8/2008 | Schwach et al. |
| 2008/0002753 A1 | 11/2008 | Neerken et al. |
| 2009/0002758 A1 | 11/2009 | Ayati et al. |
| 2010/0000167 A1 | 1/2010 | Meier |
| 2010/0010328 A1 | 1/2010 | Nguyen et al. |
| 2010/0001607 A1 | 6/2010 | Halmann et al. |
| 2010/0002495 A1 | 9/2010 | Shi |
| 2010/0002620 A1 | 10/2010 | Smith et al. |
| 2011/0021890 A1 | 1/2011 | Nishizawa et al. |
| 2011/0060229 A1 * | 3/2011 | Hulvershorn ........ A61B 5/0215 |
| | | 600/561 |
| 2011/0001664 A1 | 7/2011 | Blaivas et al. |
| 2012/0000045 A1 | 1/2012 | Gardi et al. |
| 2012/0002031 A1 | 8/2012 | Kim |
| 2012/0002261 A1 | 9/2012 | Tashiro et al. |
| 2012/0002531 A1 | 10/2012 | Okamura et al. |
| 2013/0001441 A1 | 6/2013 | Specht et al. |
| 2014/0000884 A1 | 3/2014 | Poland |
| 2014/0001487 A1 | 5/2014 | Yao et al. |
| 2014/0001717 A1 | 6/2014 | Stigall |
| 2014/0001801 A1 | 6/2014 | Tsuruno |
| 2014/0171770 A1 | 6/2014 | Hann |
| 2014/0343398 A1 | 11/2014 | He et al. |
| 2014/0003580 A1 | 12/2014 | Prater et al. |
| 2015/0000118 A1 | 1/2015 | Ahn et al. |
| 2015/0000456 A1 | 2/2015 | Smith et al. |
| 2015/0000659 A1 | 3/2015 | Maguire et al. |
| 2015/0000807 A1 | 3/2015 | Hyun et al. |
| 2015/0157216 A1 * | 6/2015 | Stigall ............... A61M 25/0045 |
| | | 600/486 |
| 2015/0190587 A1 | 7/2015 | Peh et al. |
| 2015/0003425 A1 | 12/2015 | Takeda |
| 2017/0001889 A1 | 7/2017 | Kim |
| 2018/0321181 A1 | 11/2018 | Holmstrom et al. |
| 2021/0204818 A1 | 7/2021 | Akins et al. |

FOREIGN PATENT DOCUMENTS

| | | |
|---|---|---|
| WO | 17149350 A1 | 9/2017 |
| WO | 2018219842 A1 | 12/2018 |
| WO | 2019228991 A1 | 12/2019 |
| WO | 2020150483 A2 | 7/2020 |
| WO | 2020186153 A1 | 9/2020 |

OTHER PUBLICATIONS

EP 20798430.3 filed Nov. 3, 2021 Extended European Search Report dated Jul. 27, 2023.

* cited by examiner

PUNCTURING DEVICES, PUNCTURING SYSTEMS INCLUDING THE PUNCTURING DEVICES, AND METHODS THEREOF

PRIORITY

This application claims the benefit of priority to U.S. Provisional Application No. 62/841,501, filed May 1, 2019, which is incorporated by reference in its entirety into this application.

BACKGROUND

Differentiating between a vein and an artery before placing a catheter is important as cannulating an artery is undesirable. Disclosed herein are puncturing devices, puncturing systems including the puncturing devices, and methods thereof for differentiating between a venipuncture and an arterial puncture.

SUMMARY

Disclosed herein is a puncturing device configured to differentiate between a venipuncture and an arterial puncture by way of a first type of oxygen sensor. The puncturing device includes, in some embodiments, a needle, a hub disposed over the needle, and an oxygen sensor integrated with the hub. The needle includes a shaft, a lumen defined by an inner diameter of the shaft, and a tip in a distal-end portion of the shaft. The hub is disposed over a proximal-end portion of the shaft. The hub includes a blood-flashback chamber in fluid communication with the lumen of the needle. The blood-flashback chamber is configured to capture an aliquot of blood therein at a time of accessing a vein or an artery of a patient by way of a puncture with the needle. The oxygen sensor is configured to measure oxygen in any captured blood in the blood-flashback chamber for subsequently determining a concentration of the oxygen in the captured blood, compare the concentration of the oxygen in the captured blood to that expected for venous blood or arterial blood, and indicate whether the captured blood is venous blood or arterial blood to differentiate between a venipuncture and an arterial puncture, respectively.

In some embodiments, the oxygen sensor is an electrochemical sensor including an anode and a cathode disposed in an electrolyte separated from the blood-flashback chamber by a semipermeable membrane.

In some embodiments, the semipermeable membrane is configured to allow the oxygen in the captured blood to permeate across the semipermeable membrane for electrochemical reduction of the oxygen at the cathode. Reduction of the oxygen at the cathode produces a measurable current proportional to a partial pressure of the oxygen in the captured blood.

In some embodiments, the electrochemical sensor is coupled to an external meter. The meter is configured to determine the concentration of the oxygen in the captured blood from the measurable current, compare the concentration of the oxygen in the captured blood to that expected for venous blood or arterial blood, and indicate whether the captured blood is venous blood or arterial blood to differentiate between a venipuncture and an arterial puncture, respectively.

Also disclosed herein is a puncturing system configured to differentiate between a venipuncture and an arterial puncture by way of a second type of oxygen sensor. The puncturing system includes, in some embodiments, a puncturing device and an external meter. The puncturing device includes a needle and a hub disposed over the needle. The needle includes a shaft, a lumen defined by an inner diameter of the shaft, and a tip in a distal-end portion of the shaft. The hub is disposed over a proximal-end portion of the shaft. The hub includes a blood-flashback chamber in fluid communication with the lumen of the needle. The blood-flashback chamber is configured to capture an aliquot of blood therein at a time of accessing a vein or an artery of a patient by way of a puncture with the needle. The meter includes an oxygen sensor configured for placement about the blood-flashback chamber of the puncturing device. The oxygen sensor is configured to measure oxygen in any captured blood in the blood-flashback chamber for subsequently determining a concentration of the oxygen in the captured blood, comparing the concentration of the oxygen in the captured blood to that expected for venous blood or arterial blood, and indicating whether the captured blood is venous blood or arterial blood to differentiate between a venipuncture and an arterial puncture, respectively.

In some embodiments, the oxygen sensor is an optical sensor including a red light-emitting diode ("LED") disposed in an LED housing of the meter, an infrared LED disposed in the LED housing, and a photodetector disposed in a photodetector housing of the meter opposite the an LED housing.

In some embodiments, the meter is configured to determine the concentration of the oxygen in the captured blood from a lookup table using red-light and infrared-light absorbance measurements, compare the concentration of the oxygen in the captured blood to that expected for venous blood or arterial blood, and indicate whether the captured blood is venous blood or arterial blood to differentiate between a venipuncture and an arterial puncture, respectively.

Also disclosed herein is a puncturing device configured to differentiate between a venipuncture and an arterial puncture by way of a third type of oxygen sensor. The puncturing device includes, in some embodiments, a needle, a hub disposed over the needle, and an oxygen sensor integrated with the hub. The needle includes a shaft, a lumen defined by an inner diameter of the shaft, and a tip in a distal-end portion of the shaft. The hub is disposed over a proximal-end portion of the shaft. The hub includes a blood-flashback chamber in fluid communication with the lumen of the needle. The blood-flashback chamber is configured to capture an aliquot of blood therein at a time of accessing a vein or an artery of a patient by way of a puncture with the needle. The oxygen sensor is configured to indicate a concentration of oxygen in any captured blood in the blood-flashback chamber for subsequently determining whether the concentration of the oxygen in the captured blood is consistent with venous blood or arterial blood to differentiate between a venipuncture and an arterial puncture, respectively.

In some embodiments, the oxygen sensor is a chemical formulation disposed in the blood-flashback chamber. The formulation is configured for colorimetric indication of the concentration of the oxygen in the captured blood.

In some embodiments, the formulation includes at least a buffer and a color reagent.

In some embodiments, the buffer is an alkaline buffer and the color reagent is indigo carmine.

In some embodiments, the hub includes a simple comparator thereon for colorimetrically determining whether the concentration of the oxygen in the captured blood is consistent with venous blood or arterial blood.

Also disclosed herein is a puncturing system configured to differentiate between a venipuncture and an arterial puncture by way of impedance. The puncturing system includes, in some embodiments, a puncturing device and an external meter. The puncturing device includes a needle, a hub disposed over the needle, and at least a pair of electrodes disposed in the needle. The needle includes a shaft, a lumen defined by an inner diameter of the shaft, and a tip in a distal-end portion of the shaft. The hub is disposed over a proximal-end portion of the shaft. The pair of electrodes is disposed in the shaft configured to apply and detect small electrical currents for measuring impedance of any blood in the shaft. The meter is coupled to the pair of electrodes. The meter is configured to determine impedance from electrical resistivity of any blood in the shaft, compare the impedance to that expected for venous blood or arterial blood, and indicate whether the impedance is consistent with venous blood or arterial blood to differentiate between a venipuncture and an arterial puncture, respectively.

Also disclosed herein is a puncturing system configured to differentiate between a venipuncture and an arterial puncture by way of a pressure sensor. The puncturing system includes, in some embodiments, a puncturing device and an external meter. The puncturing device includes a needle, a hub disposed over the needle, and a pressure sensor disposed in the needle. The needle includes a shaft, a lumen defined by an inner diameter of the shaft, and a tip in a distal-end portion of the shaft. The hub is disposed over a proximal-end portion of the shaft. The pressure sensor is disposed in the shaft configured to respond to changes in pressure resulting from any blood upon entering the shaft. The meter is coupled to the pressure sensor. The meter is configured to determine mean blood pressure from the changes in pressure received from the pressure sensor, compare the mean blood pressure to that expected for venous blood or arterial blood, and indicate whether the mean blood pressure is consistent with venous blood or arterial blood to differentiate between a venipuncture and an arterial puncture, respectively.

In some embodiments, the pressure sensor is a microelectromechanical system having a deformable diaphragm over a non-deformable substrate, thereby forming a capacitor responsive to the changes in pressure. The pressure sensor is configured to send to the meter changes in capacitance corresponding to the changes in pressure as the changes in pressure.

Also disclosed herein is a method for differentiating between a venipuncture and an arterial puncture. The method includes, in some embodiments, accessing a vein or an artery of a patient by way of a puncture with a puncturing device; and consulting a puncture-differentiation means for differentiating between a venipuncture and an arterial puncture, the puncture-differentiating means including an oxygen sensor for measuring oxygen in any blood captured in a blood-flashback chamber of the puncturing device, a pair of electrodes for measuring impedance of any blood in a needle of the puncturing device, or a pressure sensor for measuring changes in pressure resulting from any blood entering the needle. The puncturing device includes the needle and a hub disposed over the needle. The needle includes a shaft, a lumen defined by an inner diameter of the shaft, and a tip in a distal-end portion of the shaft. The hub is disposed over a proximal-end portion of the shaft. The hub includes the blood-flashback chamber in fluid communication with the lumen of the needle configured to capture an aliquot of blood in the blood-flashback chamber at a time of accessing a vein or an artery of a patient by way of a puncture with the needle.

In some embodiments, the method further includes determining by the puncture-differentiation means a concentration of the oxygen in the captured blood with an electrochemical sensor using measurements of current produced by electrochemical reduction of the oxygen at a cathode of the electrochemical sensor; comparing by with the puncture-differentiation means the concentration of the oxygen in the captured blood to that expected for venous blood or arterial blood; and indicating by the puncture-differentiation means whether the captured blood is venous blood or arterial blood, thereby differentiating between a venipuncture and an arterial puncture, respectively.

In some embodiments, the method further includes determining by the puncture-differentiation means a concentration of the oxygen in the captured blood with an optical sensor using red-light and infrared-light absorbance measurements by a photodetector of the optical sensor; comparing by the puncture-differentiation means the concentration of the oxygen in the captured blood to that expected for venous blood or arterial blood; and indicating by the puncture-differentiation means whether the captured blood is venous blood or arterial blood, thereby differentiating between a venipuncture and an arterial puncture, respectively.

In some embodiments, the method further includes determining by the puncture-differentiation means impedance from electrical resistivity of any blood between a pair of electrodes disposed in the shaft of the needle; comparing by the puncture-differentiation means the impedance to that expected for venous blood or arterial blood; and indicating by the puncture-differentiation means whether the impedance is consistent with venous blood or arterial blood, thereby differentiating between a venipuncture and an arterial puncture, respectively.

In some embodiments, the method further includes determining by the puncture-differentiation a mean blood pressure from any blood entering the shaft of the needle by changes in capacitance of a microelectromechanical pressure sensor disposed in the shaft; comparing by the puncture-differentiation means the mean blood pressure to that expected for venous blood or arterial blood; and indicating by the puncture-differentiation means whether the mean blood pressure is consistent with venous blood or arterial blood, thereby differentiating between a venipuncture and an arterial puncture, respectively.

These and other features of the concepts provided herein will become more apparent to those of skill in the art in view of the accompanying drawings and following description, which disclose particular embodiments of such concepts in greater detail.

DESCRIPTION

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or a "proximal end portion" of, for example, a catheter disclosed herein includes a portion of the catheter intended to be near a clinician when the catheter is used on a patient. Likewise, a "proximal length" of, for example, the catheter includes a length of the catheter intended to be near the clinician when the catheter is used on the patient. A "proximal end" of, for example, the catheter includes an end of the catheter intended to be near the clinician when the catheter is used on the patient. The proximal portion, the proximal end portion, or the proximal length of the catheter can include the proximal end of the catheter; however, the proximal portion, the proximal end portion, or the proximal length of the catheter need not include the proximal end of the catheter. That is, unless context suggests otherwise, the proximal portion, the proximal end portion, or the proximal length of the catheter is not a terminal portion or terminal length of the catheter.

With respect to "distal," a "distal portion" or a "distal end portion" of, for example, a catheter disclosed herein includes a portion of the catheter intended to be near or in a patient when the catheter is used on the patient. Likewise, a "distal length" of, for example, the catheter includes a length of the catheter intended to be near or in the patient when the catheter is used on the patient. A "distal end" of, for example, the catheter includes an end of the catheter intended to be near or in the patient when the catheter is used on the patient. The distal portion, the distal end portion, or the distal length of the catheter can include the distal end of the catheter; however, the distal portion, the distal end portion, or the distal length of the catheter need not include the distal end of the catheter. That is, unless context suggests otherwise, the distal portion, the distal end portion, or the distal length of the catheter is not a terminal portion or terminal length of the catheter.

Unless defined otherwise, all technical and scientific terms used herein have the same meaning as commonly understood by those of ordinary skill in the art.

Figure 1:
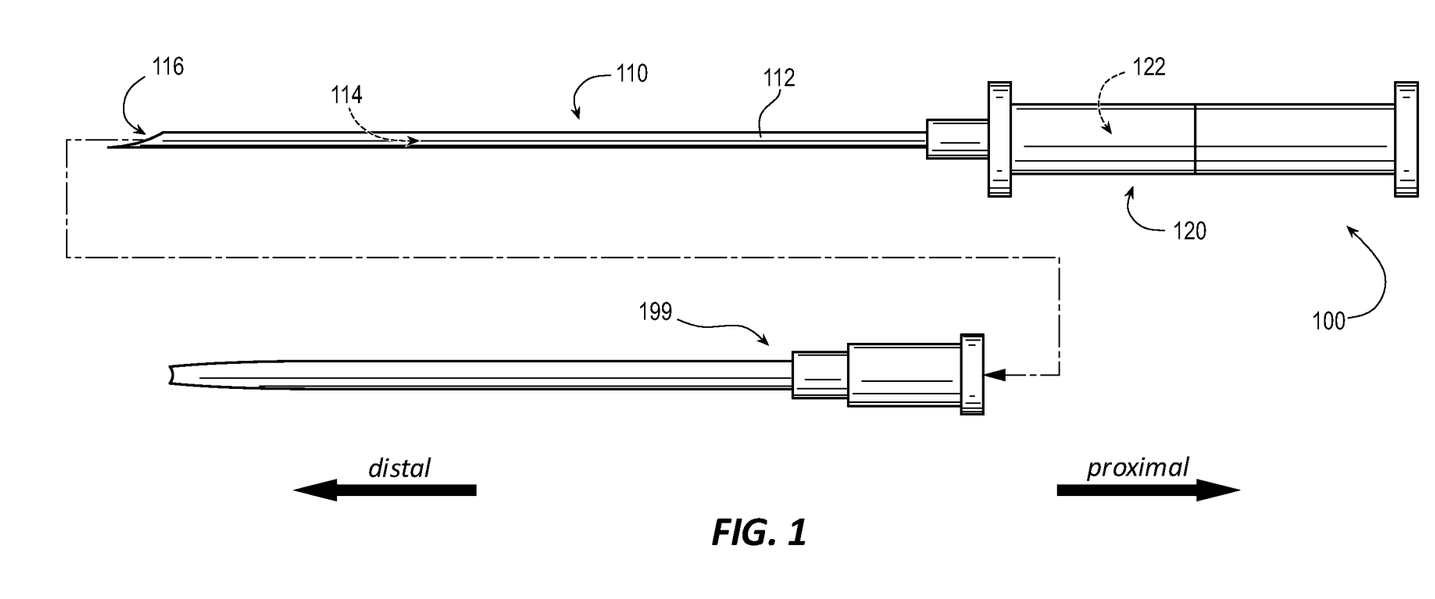
FIG. 1 illustrates a puncturing device and a catheter in accordance with some embodiments.
Figure 2:
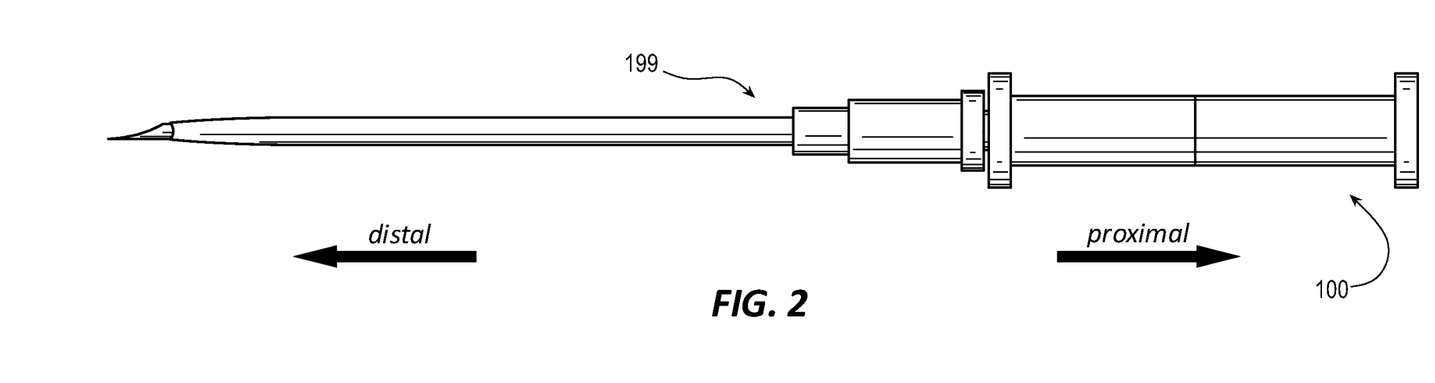
FIG. 2 illustrates the catheter of FIG. 1 disposed over the puncturing device in accordance with some embodiments.

FIG. 1 illustrates a puncturing device 100 and a catheter 199 in accordance with some embodiments. FIG. 2 illustrates the catheter 199 disposed over the puncturing device 100 in accordance with some embodiments.

As shown, the puncturing device 100 includes a needle 110 and a hub 120. The needle 110 includes a shaft 112, a lumen 114 defined by an inner diameter of the shaft 112, and a tip 116 in a distal-end portion of the shaft 112. The hub 120 is disposed over a proximal-end portion of the shaft 112. The hub 120 includes a blood-flashback chamber 122 in fluid communication with the lumen 114 of the needle 110 configured to capture an aliquot of blood in the blood-flashback chamber 122 at a time of accessing a vein or an artery of a patient by way of a puncture with the needle. The blood-flashback chamber 122 is configured to be clear such that a clinician can visualize any captured blood in the blood-flashback chamber. When present, the captured blood indicates successful entry of the punctuating device 100 in a blood vessel of the patient; however, a type of the blood vessel such as a vein or an artery is not indicated by the captured blood in the blood-flashback chamber 122 alone. For this reason, puncturing devices, puncturing systems including the puncturing devices, and methods thereof are set forth below for differentiating between puncturing a vein (i.e., a venipuncture) and an artery (i.e., an arterial puncture). Such puncturing devices are configured to allow catheters such as the catheter 199 to be disposed thereover without interference.

Blood Oxygen-Sensing Devices and Systems

Due to a relatively large difference in blood oxygen between venous blood and arterial blood, blood oxygen-sensing devices and systems including such devices are useful for differentiating between a venipuncture and an arterial puncture.

Figure 3:
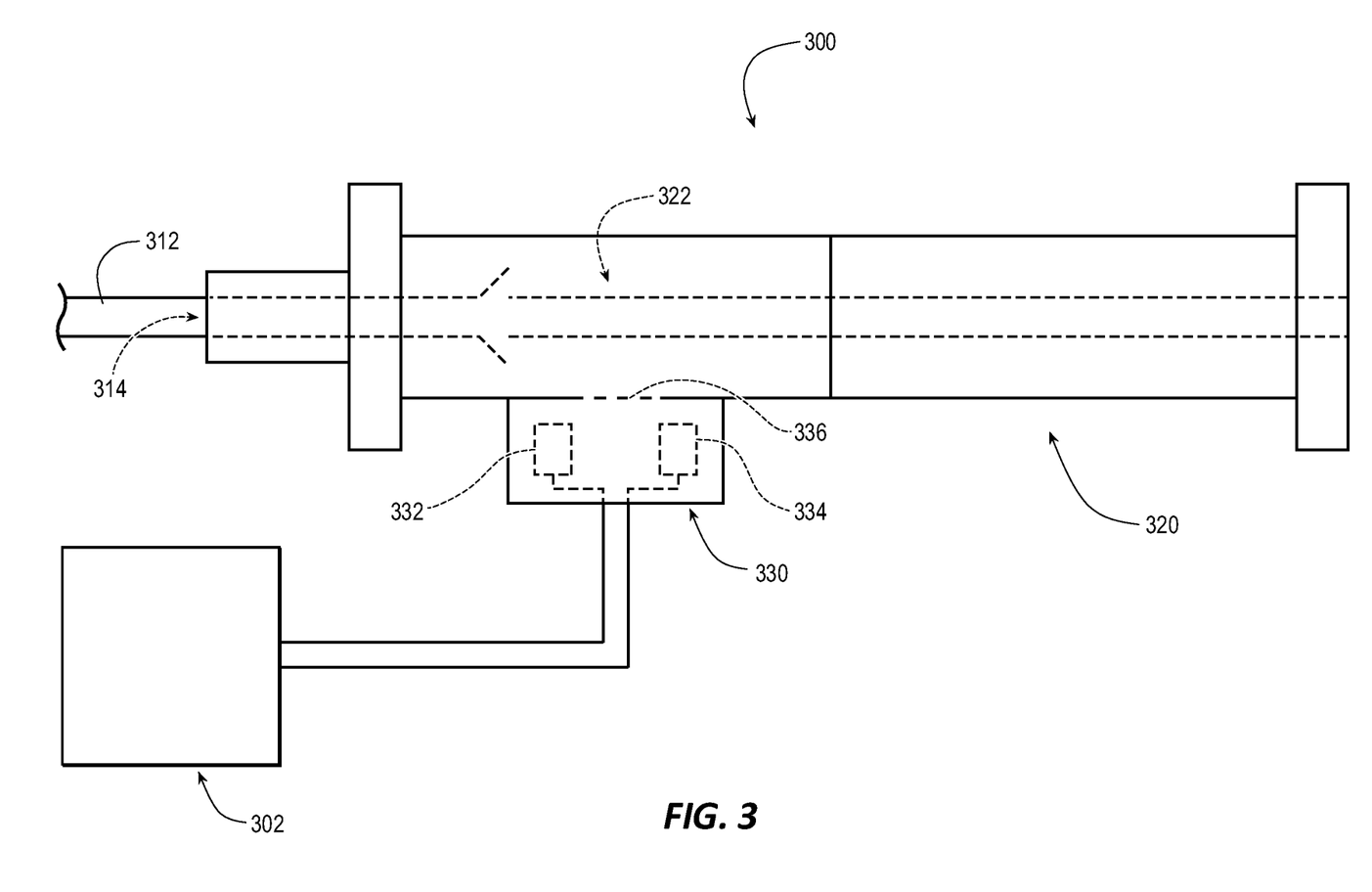
FIG. 3 illustrates a puncturing device including a first type of oxygen sensor in accordance with some embodiments.

FIG. 3 illustrates a puncturing device 300 including a first type of oxygen sensor in accordance with some embodiments. The puncturing device 300 is configured to differentiate between a venipuncture and an arterial puncture by way of the first type of oxygen sensor as set forth below.

As shown, the puncturing device 300 includes a needle such as the needle 110, a hub 320 disposed over the needle, and an oxygen sensor 330 integrated with the hub 320. The needle includes a shaft 312, a lumen 314 defined by an inner diameter of the shaft 312, and a tip such as the tip 116 of the needle 110 in a distal-end portion of the shaft 312. The hub 320 is disposed over a proximal-end portion of the shaft 312. The hub 320 includes a blood-flashback chamber 322 in fluid communication with the lumen 314 of the needle. The blood-flashback chamber 322 is configured to capture an aliquot of blood therein at a time of accessing a vein or an artery of a patient by way of a puncture with the needle. The oxygen sensor 330 is configured to measure oxygen in any captured blood in the blood-flashback chamber 322 for subsequently determining a concentration of the oxygen in the captured blood, comparing the concentration of the oxygen in the captured blood to that expected for venous blood or arterial blood, and indicating whether the captured blood is venous blood or arterial blood to differentiate between a venipuncture and an arterial puncture, respectively.

The oxygen sensor 330 is an electrochemical sensor including an anode 332 and a cathode 334 disposed in an electrolyte separated from the blood-flashback chamber 322 by a semipermeable membrane 336. If the oxygen sensor 330 is configured as a polarographic oxygen sensor, the anode 332 is silver, the cathode 334 is a noble metal such as gold or platinum, and the electrolyte is aqueous potassium chloride. If the oxygen sensor 330 is configured as a galvanic oxygen sensor, the anode 332 is zinc, lead, or another active metal, the cathode 334 is nickel or a noble metal such silver, and the electrolyte is aqueous sodium chloride or sodium hydroxide. Whether the oxygen sensor 330 is polarographic oxygen sensor or a galvanic oxygen sensor, the semipermeable membrane 336 is configured to allow the oxygen in the captured blood to permeate across the semipermeable membrane 336 for electrochemical reduction of the oxygen at the cathode 334. Reduction of the oxygen at the cathode 334 produces a measurable current proportional to a partial pressure of the oxygen in the captured blood.

The electrochemical sensor can be coupled to an external meter 302, which can be optionally integrated with an ultrasound transducer, thereby forming a puncturing system including the puncturing device 300. The meter 302 can be configured with an algorithm in a memory thereof to determine the concentration of the oxygen in the captured blood from the foregoing measurable current. The meter 302 can be configured with another algorithm in the memory to compare the concentration of the oxygen in the captured blood to that expected for venous blood or arterial blood. The meter 302 can be configured with a display (not shown) to indicate whether the captured blood is venous blood or arterial blood to differentiate between a venipuncture and an arterial puncture, respectively. For at least the polarographic oxygen sensor, the meter 302 can also be configured to supply a current to the electrochemical sensor 330 for maintaining a constant potential across the anode 332 and the cathode 334 for the electrochemical reduction of the oxygen at the cathode 334.

Figure 4:
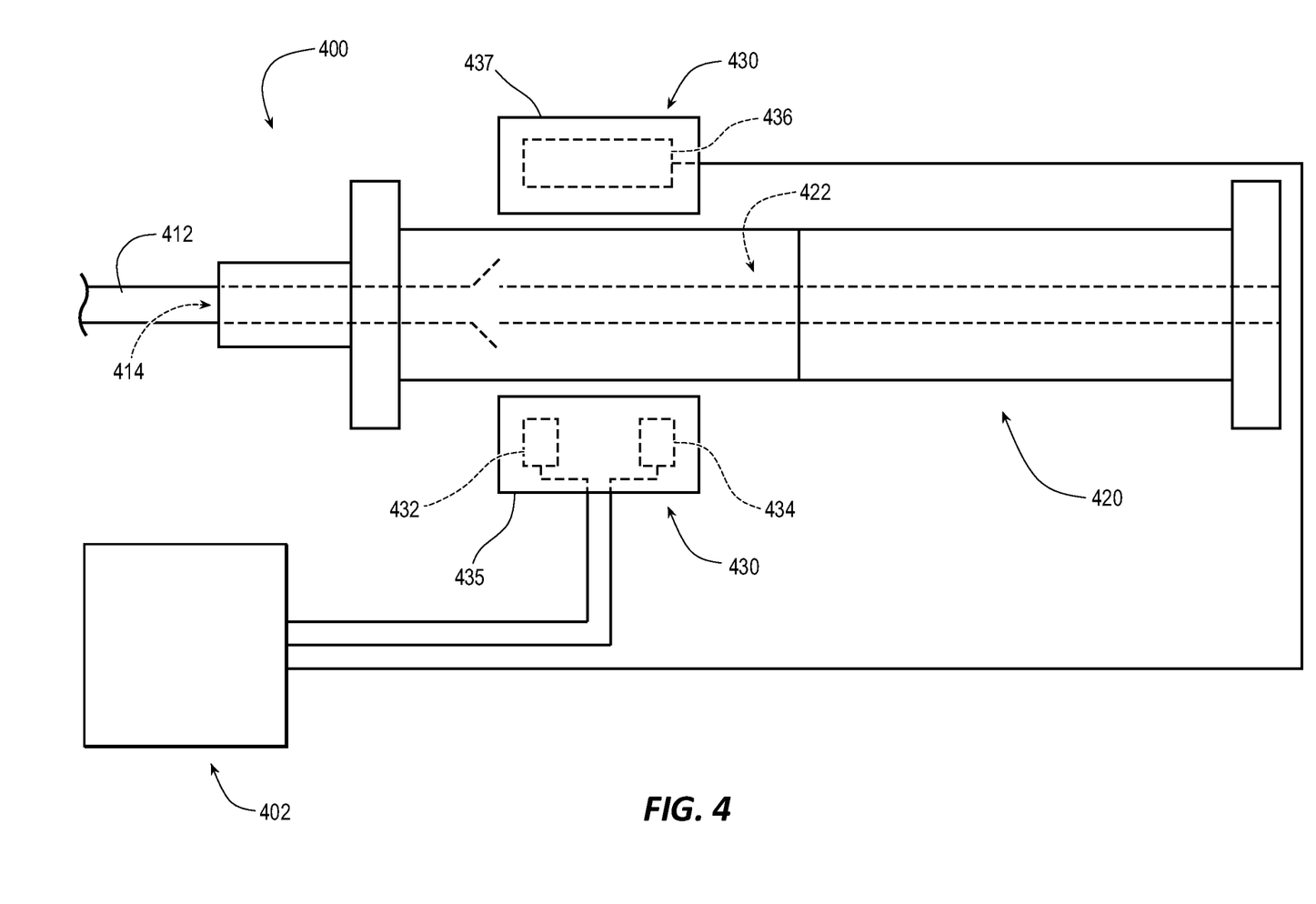
FIG. 4 illustrates a puncturing system including a second type of oxygen sensor in accordance with some embodiments.

FIG. 4 illustrates a puncturing system including a second type of oxygen sensor in accordance with some embodiments. The puncturing system is configured to differentiate between a venipuncture and an arterial puncture with a puncturing device 400 by way of the second type of oxygen sensor as set forth below.

As shown, the puncturing system includes the puncturing device 400 and an external meter 402. The puncturing device 400 includes a needle such as the needle 110 and a hub 420 disposed over the needle. The needle includes a shaft 412, a lumen 414 defined by an inner diameter of the shaft 412, and a tip such as the tip 116 of the needle 110 in a distal-end portion of the shaft 412. The hub 420 is disposed over a proximal-end portion of the shaft 412. The hub 420 includes a blood-flashback chamber 422 in fluid communication with the lumen 414 of the needle. The blood-flashback chamber 422 is configured to capture an aliquot of blood therein at a time of accessing a vein or an artery of a patient by way of a puncture with the needle. The meter 402 includes an oxygen sensor 430 configured for placement about the blood-flashback chamber 422 of the puncturing device 400. The oxygen sensor 430 is configured to measure oxygen in any captured blood in the blood-flashback chamber 422 for subsequently determining a concentration of the oxygen in the captured blood, comparing the concentration of the oxygen in the captured blood to that expected for venous blood or arterial blood, and indicating whether the captured blood is venous blood or arterial blood to differentiate between a venipuncture and an arterial puncture, respectively.

The oxygen sensor 430 is an optical sensor including a red LED 432 disposed in an LED housing 435 of the meter 402, an infrared LED 434 disposed in the LED housing 435, and a photodetector 436 disposed in a photodetector housing 437 of the meter opposite the LED housing. Optionally, the LED housing 435 and the photodetector housing 437 are of the same housing, which is configured with a 'C' shape for cradling the blood-flashback chamber 422 of the puncturing device 400. Oxygenated hemoglobin in blood such as the captured blood absorbs more infrared light and allows more red light to pass through than deoxygenated (or reduced) hemoglobin, which absorbs more red light and allows more infrared light to pass through. As such, the LED 432 is configured to emit red light at an optimized 600-750 nm wavelength, whereas the LED 434 is configured to emit infrared light in an optimized 850-1000 nm wavelength. Optionally, the function of the LED 432 and the LED 434 is embodied in a single LED configured to emit the red light and the infrared light at different times.

The meter 402, which can be optionally integrated with an ultrasound transducer, can be configured with an algorithm in a memory thereof configured to determine the concentration of the oxygen in the captured blood from a lookup table in the memory using red-light and infrared-light absorbance measurements provided by the photodetector 436. The meter 402 can be configured with another algorithm in the memory to compare the concentration of the oxygen in the captured blood to that expected for venous blood or arterial blood. The meter 302 can be configured with a display (not shown) to indicate whether the captured blood is venous blood or arterial blood to differentiate between a venipuncture and an arterial puncture, respectively.

Figure 5:
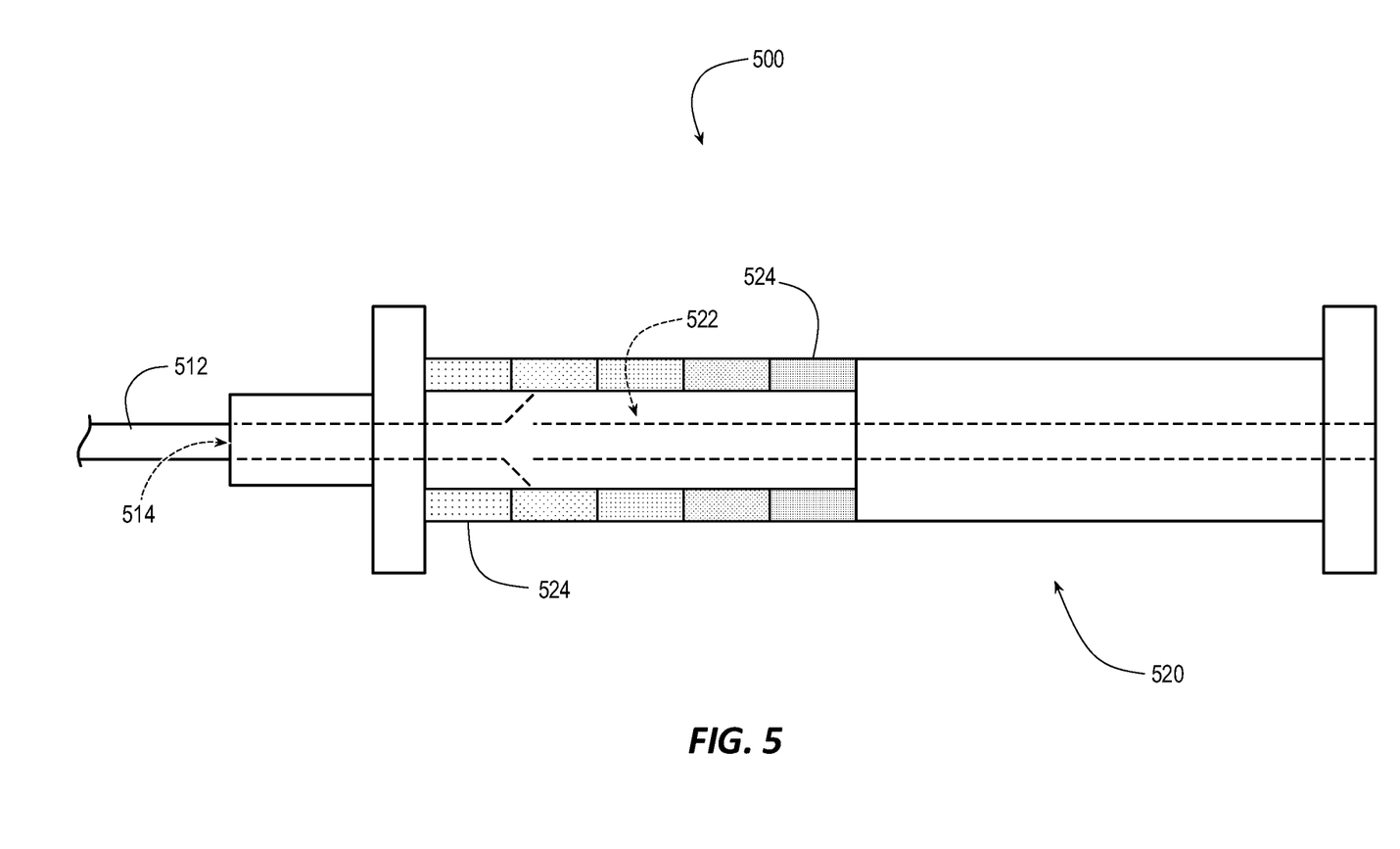
FIG. 5 illustrates a puncturing device including a third type of oxygen sensor in accordance with some embodiments.

FIG. 5 illustrates a puncturing device 500 including a third type of oxygen sensor in accordance with some embodiments. The puncturing device 500 is configured to differentiate between a venipuncture and an arterial puncture by way of the third type of oxygen sensor as set forth below.

As shown, the puncturing device includes a needle such as the needle 110, a hub 520 disposed over the needle, and an oxygen sensor integrated with the hub 520. The needle includes a shaft 512, a lumen 514 defined by an inner diameter of the shaft 514, and a tip such as the tip 116 of the needle 110 in a distal-end portion of the shaft 512. The hub 520 is disposed over a proximal-end portion of the shaft 512. The hub 520 includes a blood-flashback chamber 522 in fluid communication with the lumen 514 of the needle. The blood-flashback chamber 522 is configured to capture an aliquot of blood therein at a time of accessing a vein or an artery of a patient by way of a puncture with the needle. The oxygen sensor is configured to indicate a concentration of oxygen in any captured blood in the blood-flashback chamber 520 for a user such as a clinician to subsequently determining whether the concentration of the oxygen in the captured blood is consistent with venous blood or arterial blood to differentiate between a venipuncture and an arterial puncture, respectively.

The oxygen sensor is a chemical formulation disposed in the blood-flashback chamber 520. The formulation is configured for colorimetric indication of the concentration of the oxygen in the captured blood. The formulation includes at least a color reagent and a buffer configured to keep the color reagent within a specific pH range over which the color reagent is operable. The color reagent can be indigo carmine and the buffer can be an alkaline buffer configured to keep the indigo carmine between a pH of about 8 to 9.

The hub 520 can include a simple comparator 524 printed thereon for the user to colorimetrically determine whether the concentration of the oxygen in the captured blood is consistent with venous blood or arterial blood. Optionally, the simple comparator 524 is provided on a piece of paper or paperboard provided with the puncturing device 500.

Impedance-Based Devices and Systems

While the difference in impedance between venous blood and arterial blood might be relatively small, impedance-based devices and systems including such devices are useful for differentiating between a venipuncture and an arterial puncture.

Figure 6:
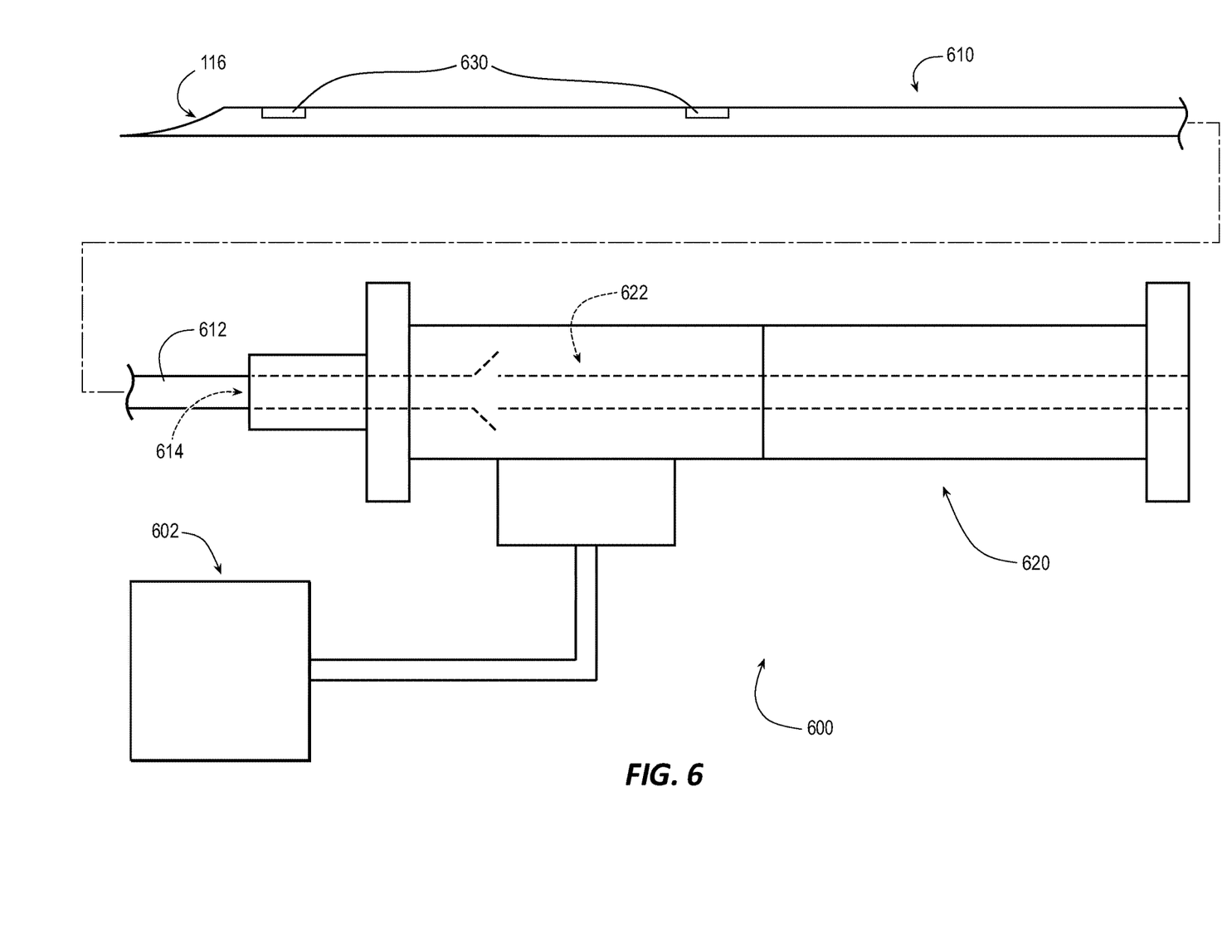
FIG. 6 illustrates an impedance-based puncturing system in accordance with some embodiments.

FIG. 6 illustrates an impedance-based puncturing system in accordance with some embodiments. The puncturing system is configured to differentiate between a venipuncture and an arterial puncture with a puncturing device 600 by way of impedance as set forth below.

As shown, the puncturing system includes the puncturing device 600 and an external meter 602. The puncturing device 600 includes a needle 610, a hub 620 disposed over the needle 610, and at least a pair of electrodes 630 disposed in the needle 610. The needle 610 includes a shaft 612, a lumen 614 defined by an inner diameter of the shaft 612, and a tip 616 of the needle 610 in a distal-end portion of the shaft 612. The hub 620 is disposed over a proximal-end portion of the shaft 612. Optionally, the hub 620 includes the blood-flashback chamber 622 in fluid communication with the lumen 614 of the needle 610, which blood-flashback chamber 622 is configured to capture an aliquot of blood therein at a time of accessing a vein or an artery of a patient by way of a puncture with the needle 610. The pair of electrodes 630 is disposed in the shaft 612 configured to apply and detect small electrical currents for measuring impedance of any blood in the shaft 612. When the blood-flashback chamber 622 is present, the pair of electrodes 630 can be alternatively disposed in the blood-flashback chamber 622 configured to apply and detect small electrical currents for measuring impedance of any blood in the blood-flashback chamber 622. The meter 602, which can be optionally integrated with an ultrasound transducer, is coupled to the pair of electrodes 630. The meter 602 can be configured with an algorithm in a memory thereof to determine impedance from electrical resistivity of any blood in the shaft 612 (or the blood-flashback chamber 622). The meter 602 can be configured with another algorithm in the memory to compare the impedance to that expected for venous blood or arterial blood. The meter 602 can be configured with a display (not shown) to indicate whether the impedance is consistent with venous blood or arterial blood to differentiate between a venipuncture and an arterial puncture, respectively.

Blood Pressure-Sensing Devices and Systems

Figure 8:
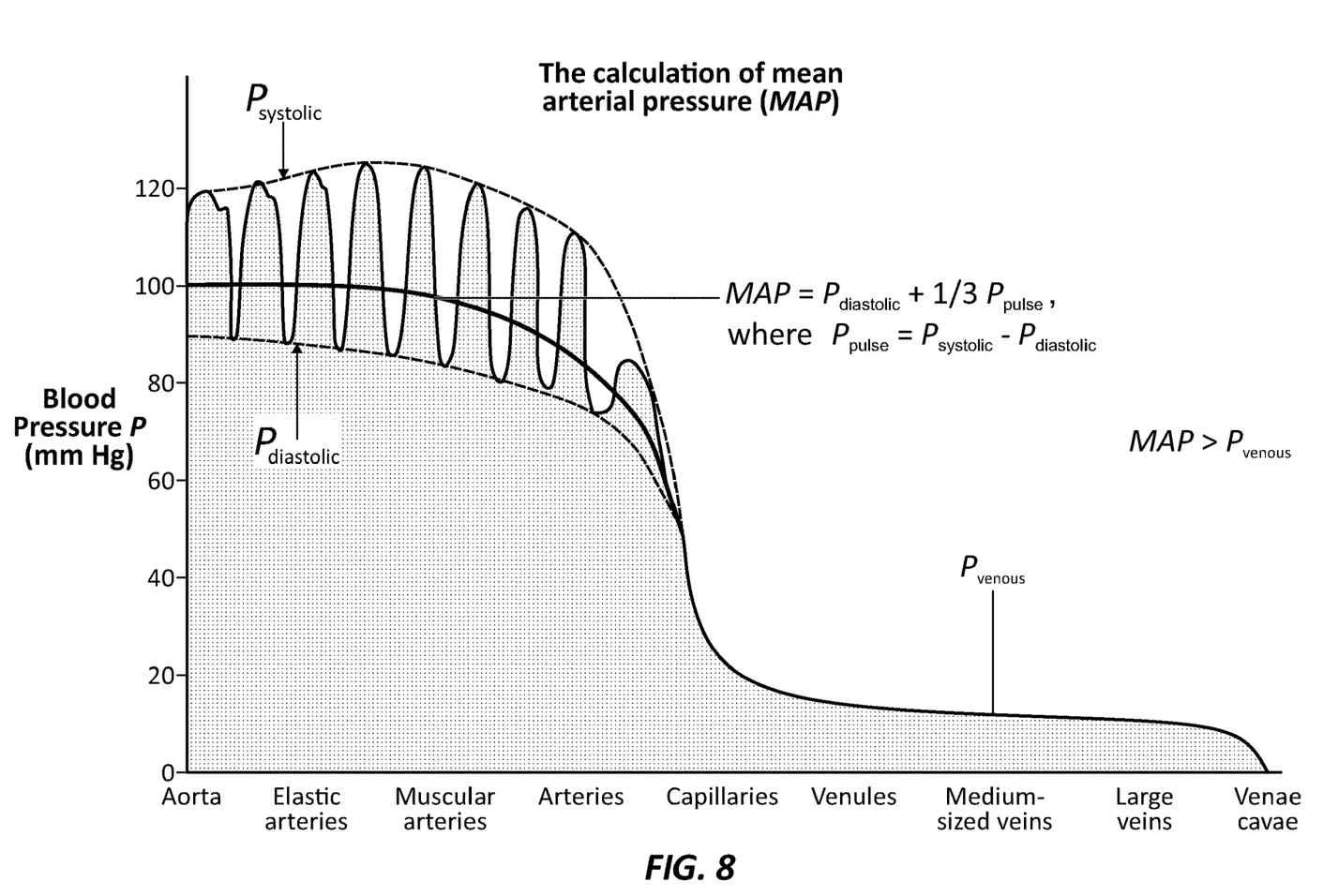
FIG. 8 illustrates mean blood pressure as a sum of a diastolic pressure and one-third of a systolic pressure in accordance with some embodiments.

Due to a relatively large difference in blood pressure P between venous blood and arterial blood as shown in FIG. 8 by comparison of venous blood pressure $P_{venous}$ and mean arterial pressure MAP, blood pressure-sensing devices and systems including such devices are useful for differentiating between a venipuncture and an arterial puncture.

Figure 7:
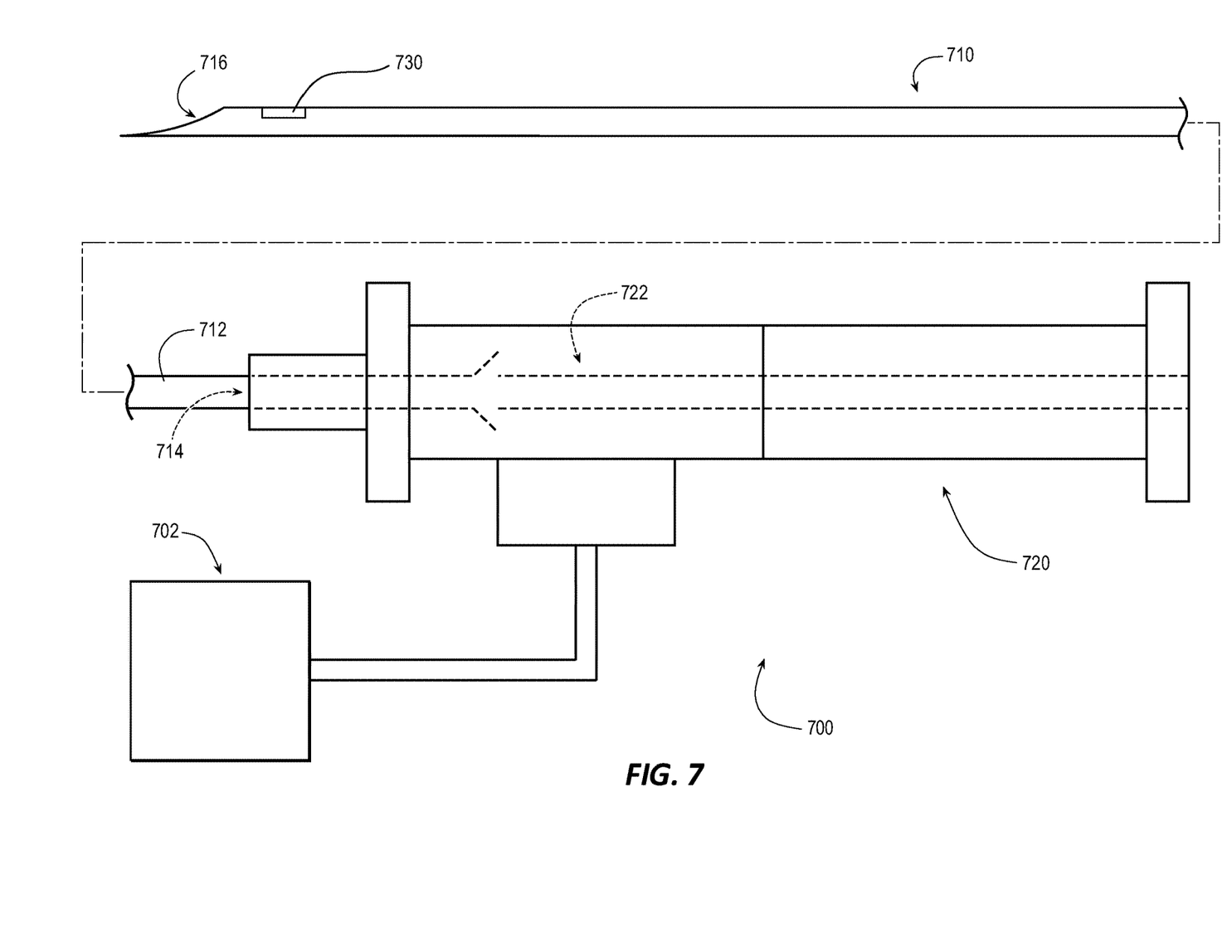
FIG. 7 illustrates a blood pressure-sensing puncturing system in accordance with some embodiments.

FIG. 7 illustrates a blood pressure-sensing puncturing system in accordance with some embodiments. The puncturing system is configured to differentiate between a venipuncture and an arterial puncture with a puncturing device 700 by way of blood pressure as set forth below.

As shown, the puncturing system includes a puncturing device 700 and an external meter 702. The puncturing device 700 includes a needle 710, a hub 720 disposed over the needle 710, and a pressure sensor 730 disposed in the needle 710. The needle 710 includes a shaft 712, a lumen 714 defined by an inner diameter of the shaft 712, and a tip 716 in a distal-end portion of the shaft 712. The hub 720 is disposed over a proximal-end portion of the shaft 712. Optionally, the hub 720 includes the blood-flashback chamber 722 in fluid communication with the lumen 714 of the needle 710, which blood-flashback chamber 722 is configured to capture an aliquot of blood therein at a time of accessing a vein or an artery of a patient by way of a puncture with the needle 710. The pressure sensor 730 is disposed in the shaft 712 configured to respond to changes in pressure resulting from any blood upon entering the shaft 712. The meter 702, which can be optionally integrated with an ultrasound transducer, is coupled to the pressure sensor 730. The meter 702 can be configured with an algorithm in a memory thereof to determine mean blood pressure from the changes in pressure received from the pressure sensor 730. The meter 702 can be configured with another algorithm in the memory to compare the mean blood pressure to that expected for venous blood or arterial blood. The meter 702 can be configured with a display (not shown) to indicate whether the mean blood pressure is consistent with venous blood or arterial blood to differentiate between a venipuncture and an arterial puncture, respectively.

The pressure sensor 730 can be a microelectromechanical system having a deformable diaphragm over a non-deformable substrate, thereby forming a capacitor responsive to the changes in pressure. The pressure sensor 730 is configured to send to the meter 702 changes in capacitance corresponding to the changes in pressure as the changes in pressure.

Methods

In view of the foregoing puncturing devices and the puncturing systems including the puncturing devices, methods for differentiating between a venipuncture and an arterial puncture are also provided.

Methods for differentiating between a venipuncture and an arterial puncture include accessing a vein or an artery of a patient by way of a puncture with the puncturing device 300, 400, 500, 600, or 700; and consulting a puncture-differentiation means for differentiating between a venipuncture and an arterial puncture, the puncture-differentiating means including the oxygen sensor 330, 430, etc. for measuring oxygen in any blood captured in the blood-flashback chamber 322, 433, or 522 of the puncturing device 300, 400, or 500, the pair of electrodes 630 for measuring impedance of any blood in the needle 610 of the puncturing device 600, or the pressure sensor 730 for measuring changes in pressure resulting from any blood entering the needle 710 of the puncturing device 700. The puncture-differentiating means includes components of any one of the puncturing device 300, 400, 500, 600, or 700 or the systems including the foregoing puncturing devices for differentiating between a venipuncture and an arterial puncture.

The method can further include determining by the algorithm in the memory of the meter 302 a concentration of the oxygen in the captured blood with the oxygen sensor 330 configured as an electrochemical sensor using measurements of current produced by electrochemical reduction of the oxygen at the cathode 334 of the electrochemical sensor; comparing by the other algorithm in the memory of the meter 302 the concentration of the oxygen in the captured blood to that expected for venous blood or arterial blood; and indicating on the display of the meter 302 whether the captured blood is venous blood or arterial blood, thereby differentiating between a venipuncture and an arterial puncture, respectively.

The method can further include determining by the algorithm in the memory of the meter 402 a concentration of the oxygen in the captured blood with the oxygen sensor 430 configured as an optical sensor using red-light and infrared-light absorbance measurements by the photodetector 436 of the optical sensor; comparing by the other algorithm in the memory of the meter 402 the concentration of the oxygen in the captured blood to that expected for venous blood or arterial blood; and indicating on the display of the meter 402 whether the captured blood is venous blood or arterial blood, thereby differentiating between a venipuncture and an arterial puncture, respectively.

The method can further include determining by the algorithm in the memory of the meter 602 impedance from electrical resistivity of any blood between the pair of electrodes 630 disposed in the shaft 612 of the needle 610; comparing by the other algorithm in the memory of the meter 602 the impedance to that expected for venous blood or arterial blood; and indicating on the display of the meter 602 whether the impedance is consistent with venous blood or arterial blood, thereby differentiating between a venipuncture and an arterial puncture, respectively.

The method can further include determining by the algorithm in the memory of the meter 702 a mean blood pressure from any blood entering the shaft 712 of the needle 710 by changes in capacitance of the microelectromechanical pressure sensor 730 disposed in the shaft 712; comparing by the other algorithm of the meter 702 the mean blood pressure to that expected for venous blood or arterial blood; and indicating on the display of the meter 702 whether the mean blood pressure is consistent with venous blood or arterial blood, thereby differentiating between a venipuncture and an arterial puncture, respectively.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. A puncturing device configured to differentiate between a venipuncture and an arterial puncture, comprising:
   a needle including a shaft, a lumen defined by an inner diameter of the shaft, and a tip in a distal-end portion of the shaft;
   a hub disposed over a proximal-end portion of the shaft, the hub including a blood-flashback chamber in fluid communication with the lumen of the needle configured to capture an aliquot of blood in the blood-flashback chamber at a time of accessing a vein or an artery of a patient by way of a puncture with the needle; and
   an oxygen sensor integrated with the hub configured to colorimetrically indicate a concentration of oxygen in captured blood in the blood-flashback chamber for subsequently determining whether the concentration of oxygen in the captured blood is consistent with venous blood or arterial blood to differentiate between a venipuncture and an arterial puncture, respectively, the oxygen sensor including a chemical formulation having an alkaline buffer and indigo carmine as a color agent disposed in the blood-flashback chamber.

2. The puncturing device according to claim 1, wherein the hub includes a comparator thereon for colorimetrically determining whether the concentration of oxygen in the captured blood is consistent with venous blood or arterial blood.

3. A puncturing system configured to differentiate between a venipuncture and an arterial puncture, comprising:
   a puncturing device including:
      a needle including a shaft, a lumen defined by an inner diameter of the shaft, and a tip in a distal-end portion of the shaft;
      a hub disposed over a proximal-end portion of the shaft; and
      a capacitive pressure sensor disposed in the shaft of the needle configured to respond to changes in pressure from blood entering the shaft, the capacitive pressure sensor being a microelectromechanical system having a deformable diaphragm over a non-deformable substrate responsive to the changes in pressure; and
   an external meter coupled to the capacitive pressure sensor configured to determine mean blood pressure from the changes in pressure received from the capacitive pressure sensor, compare the mean blood pressure to that expected for venous blood or arterial blood, and indicate whether the mean blood pressure is consistent with venous blood pressure or arterial blood pressure to differentiate between a venipuncture and an arterial puncture, respectively, the capacitive pressure sensor being configured to send to the external meter changes in capacitance corresponding to the changes in pressure.

4. A method for differentiating between a venipuncture and an arterial puncture, comprising:
   accessing a vein or an artery of a patient by way of a puncture with a puncturing device, the puncturing device including:
      a needle including a shaft, a lumen defined by an inner diameter of the shaft, and a tip in a distal-end portion of the shaft; and
      a hub disposed over a proximal-end portion of the shaft, the hub including a blood-flashback chamber in fluid communication with the lumen of the needle configured to capture an aliquot of blood in the blood-flashback chamber at a time of accessing the vein or the artery of the patient by way of the puncture with the needle;
   consulting a puncture-differentiation means for differentiating between the venipuncture and the arterial puncture, the puncture-differentiation means including a pair of electrodes disposed in the shaft of the needle for measuring impedance of any blood in the shaft;
   determining by the puncture-differentiation means impedance from electrical resistivity of the blood between the pair of electrodes disposed in the shaft of the needle;
   comparing by the puncture-differentiation means the impedance to that expected for venous blood or arterial blood; and
   indicating by the puncture-differentiation means whether the impedance is consistent with venous blood or arterial blood, thereby differentiating between the venipuncture and the arterial puncture, respectively.

5. A method for differentiating between a venipuncture and an arterial puncture, comprising:
   accessing a vein or an artery of a patient by way of a puncture with a puncturing device, the puncturing device including:
      a needle including a shaft, a lumen defined by an inner diameter of the shaft, and a tip in a distal-end portion of the shaft; and
      a hub disposed over a proximal-end portion of the shaft, the hub including a blood-flashback chamber in fluid communication with the lumen of the needle configured to capture an aliquot of blood in the blood-flashback chamber at a time of accessing the vein or the artery of the patient by way of the puncture with the needle;

consulting a puncture-differentiation means for differentiating between the venipuncture and the arterial puncture, the puncture-differentiation means including a chemical-based oxygen sensor integrated with the hub for colorimetrically indicating oxygen in any captured blood in the blood-flashback chamber;

colorimetrically indicating by the puncture-differentiation means a concentration of the oxygen in the captured blood with the chemical-based oxygen sensor using a chemical formulation disposed in the blood-flashback chamber, the chemical formulation including an alkaline buffer and indigo carmine as a color agent;

comparing the concentration of the oxygen in the captured blood colorimetrically indicated by the chemical formulation against a comparator on the hub of the puncturing device; and colorimetrically determining whether the concentration of the oxygen in the captured blood is consistent with venous blood or arterial blood.

* * * * *